US00PP17397P3

(12) United States Plant Patent
Meilland

(10) Patent No.: US PP17,397 P3
(45) Date of Patent: Feb. 6, 2007

(54) HYBRID TEA ROSE PLANT NAMED 'MEIVILITY'

(50) Latin Name: *Rosa hybrida*
Varietal Denomination: Meivility

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 19 days.

(21) Appl. No.: 11/086,744

(22) Filed: Mar. 23, 2005

(65) Prior Publication Data

US 2005/0278813 P1 Dec. 15, 2005

(30) Foreign Application Priority Data

Jun. 11, 2004 (QZ) ..... PBR20041053

(51) Int. Cl.
*A01H 5/00* (2006.01)

(52) U.S. Cl. ..... Plt./132

(58) Field of Classification Search ..... Plt./132, Plt./130

See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of Hybrid Tea rose plant is provided which abundantly forms on a continuous basis attractive very double long-lasting cream white blossoms having a strong fragrance that are slightly suffused and bordered with pink. The new variety of the present invention is a spontaneous mutation of unknown causation of the 'Meivildo' variety (U.S. Plant Pat. No. 6,895). The plant exhibits very vigorous vegetation, a semi-erect growth habit, dense medium green foliage with a semi-glossy aspect, and good tolerance to crytogamic diseases such as powdery mildew. The attractive medium green foliage contrasts nicely with the blossom coloration. The new variety is particularly well suited for growing as attractive ornamentation in parks and gardens.

1 Drawing Sheet

Botanical/commercial classification: *Rosa hybrida*/Hybrid Tea Rose Plant.
Varietal denomination: cv. Meivility.

SUMMARY OF THE INVENTION

The new variety of *Rosa hybrida* Hybrid Tea rose plant was discovered as a distinctive branch mutation at Le Cannet des Maures, Var, France, during 2002 while growing in a cultivated area among plants of the 'Meivildo' variety (U.S. Plant Pat. No. 6,895). The 'Meivildo' variety is being marketed under the YVES PIAGET trademark. I was primarily attracted to the new plant of the present invention in view of its distinctive blossom coloration. The new variety of the present invention is a spontaneous mutation of the 'Meivildo' variety of unknown causation. Had I not discovered and preserved the new plant of the present invention it would have been lost to mankind.

It was found that the new variety of the present invention:

(a) exhibits a semi-erect growth habit, (b) abundantly forms on a continuous basis attractive very double long-lasting cream white blossoms having a very strong fragrance that are slightly suffused and bordered with pink, (c) forms vigorous and dense medium green foliage having a semi-glossy aspect that contrasts well with the blossom coloration, and (d) is particularly well suited for growing as attractive ornamentation in parks and gardens.

The disease tolerance is very good with respect to crytogamic diseases such as powdery mildew.

The new variety well meets the needs of the horticultural industry and can be grown to advantage in the landscape where attractive ornamentation is desired.

The new variety can be readily distinguished from its parental 'Meivildo' variety. More specifically, the 'Meivildo' variety forms dissimilarly colored near neyron pink blossoms. This coloration is readily distinguishable from the cream white slightly suffused and bordered with pink blossom coloration of the new variety of the present invention.

The new variety also can be readily distinguished from the 'Meimagarmic' variety (U.S. Plant Pat. No. 5,067) and the 'Meiparnin' variety (U.S. Plant Pat. No. 10,477). More specifically, the blossoms of the 'Meimagarmic' variety exhibit no fragrance unlike those of the new variety, and the 'Meiparnin' variety displays a significantly taller growth habit.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another. Accordingly, the new variety of the present invention reliably undergoes asexual propagation in a true to type manner.

The new variety has been named the 'Meivility' variety.

BRIEF DESCRIPTION OF THE PHOTOGRAPH

The accompanying photograph shows as nearly true as it is reasonably possible to make the same, in a color illustration of this character a typical open blossom of the new variety. The cream white blossom coloration bordered and suffused with pink is shown. The rose plant of the new variety was approximately two years of age and was observed during May while budded on *Rosa indica* understock and growing outdoors at Le Cannet des Maures, Var, France.

DETAILED DESCRIPTION

The chart used in the identification of the colors is that of The Royal Horticultural Society (R.H.S. Colour Chart). The description is based on the observation of two year-old plants during February while budded on *Rosa indicia* understock and growing outdoors at Le Cannet des Maures, Var, France.

Plant:

*Height.*—Approximately 85 cm on average at the end of the growing season.

*Width.*—Approximately 40 cm on average at the end of the growing season.

*Habit.*—Semi-erect.

Branches:

*Color.*—Young stems: near Yellow-Green Group 146C. Adult wood: near Yellow-Green Group 146B.

*Texture.*—Young stems: smooth. Adult stems: smooth.

*Thorns.*—Quantity and size: on 12 cm of young stems approximately 4 on average having a length of approximately 0.5 cm on average, and on 10 cm of adult stems approximately 7 on average having a length of approximately 0.4 cm on average and approximately 2 small prickles on average having a length of approximately 0.2 cm on average. Color: on young stems near Yellow-Green Group 147B, and on adult stems near Greyed-Orange Group 165B at the base and near Greyed-Orange Group 165C at the tip. The prickles on the adult stems commonly are Greyed-Orange Group 165C in coloration. Configuration: rather upright and curved downwards on the upper surface, concave on the under surface, and elliptical on the base.

Leaves:

*Size.*—A seven-leaflet leaf including the petiole commonly is approximately 15.8 cm in length on average, and approximately 12 cm in width on average.

*Stipules.*—Adnate, pectinate, rather narrow, smooth, approximately 1 cm in length on average, approximately 0.15 cm in width on average, and near Yellow-Green Group 146D on the upper surface and near Yellow-Green Group 147D on the under surface.

*Petioles.*—Upper surface: smooth, and near Yellow-Green Group 146A in coloration. Under surface: smooth, and near Yellow-Green Group 146C and 146D in coloration. Length: Approximately 3.3 cm for the terminal leaflet.

*Petiole rachis.*—Upper surface: generally smooth, and near Yellow-Green Group 146A in coloration. Under surface: glandular, with some prickles, and near Yellow-Green Group 146C and 146D in coloration.

*Leaflets.*—Number: 3, 5 and 7 (most often). Shape: generally elliptic with a rounded base and a symmetrical tip. Size: the terminal leaflets commonly are approximately 6.5 cm in length on average and approximately 4.5 cm in width on average. Margin: denticulate. Serration: simple and regular. Texture: physically firm and leathery. General appearance: ample, dense, and medium green with a semi-glossy aspect. Color (young foliage): Upper surface: near Yellow-Green Group 146A. Under surface: near Yellow-Green Group 146B. Color (adult foliage): Upper surface: near Yellow-Green Group 147A. Under surface: near Yellow-Green Group 147B.

Inflorescence:

*Number of flowers.*—Between 1 and 3 per stem, and commonly one per stem.

*Peduncle.*—Glandular, firm and of good strength, near Yellow-Green Group 144B in coloration, approximately 4 cm in length on average, and approximately 0.3 cm in diameter on average.

*Sepals.*—Upper surface: tomentose and near Greyed-Green Group 194A in coloration. Under surface: glandular with very weak extensions, and near Yellow-Green Group 146A in coloration. Configuration: longish-pointed and narrow at the tip. Size: Approximately 2.6 cm in length and approximately 1.1 cm in width at the widest point.

*Buds.*—Shape: globular. Size: fairly large. Length: approximately 4 cm in length and width on average.

*Flower.*—Shape: initially globular changing to cup-shaped. Diameter: approximately 13 cm on average. Color (during course of opening): Upper surface: near White Group 155A and slightly suffused with Red Group 55B and 55C and edged with Red Group 51A. Under surface: near White Group 155A and slightly suffused with Red Group 55B and 55C and edged with Red Group 51A. Basal petal spot: upper surface: near Yellow Group 2B. Under surface: near Yellow Group 2D. Color (open flower): Upper surface: near White Group 155A and slightly suffused on the margin with Red Group 55C and edged with Red Group 55B. Under surface: near White Group 155A and slightly suffused on the margin with Red Group 55C and edged with Red Group 55B. Basal petal spot: upper surface: near Yellow Group 2B. Under surface: near Yellow Group 2D. Petaloids: approximately 7 on average per flower, commonly approximately 1.4 to 2 cm in length on average, and near Red Group 55B and 55C in coloration. Color stability: slight change in color upon the passage of time. Fragrance: very strong. Lasting quality: long, commonly approximately 12 to 14 days on average on the plant and approximately 9 to 10 days on average when cut and placed in a vase. Petal number: approximately 80 on average under normal growing conditions. Petal shape: rounded with broad crenation at edge resembling somewhat that of a peony. Petal texture: firm. Petal length: approximately 4.2 cm on average. Petal width: approximately 4 cm on average. Petal arrangement: imbricated with petaloids at the center. Petal drop: good with the petals commonly detaching cleanly before drying. Stamen number: approximately 93 on average. Anthers: regularly arranged around the styles, approximately 0.3 cm in size on average, and near Greyed-Orange Group 167A in coloration. Filaments: approximately 0.8 cm in length on average, and near Yellow-Group 7C in coloration. Pistils: approximately 73 on average. Stigmas: approximately 0.1 cm in size on average and near Yellow Group 10B in coloration. Styles: approximately 0.6 cm in length on average, and near Greyed-Green Group 190D in coloration. Receptacle: smooth, pear-shaped in longitudinal section, approximately 1.4 cm in length on average, approximately 1.5 cm in width on average at the widest point, and near Yellow-Green Group 144B in coloration. Hips: none observed.

Development:

*Vegetation.*—Very vigorous.

*Blooming.*—Abundant and continuous.

*Resistance to diseases.*—Very good tolerance to crytogamic diseases such as powdery mildew.

*Aptitude to bear fruit.*—None observed.

*Resistance to cold.*—U.S.D.A. Hardiness Zone No. 6A.

*Resistance to heat.*—Grows well during a summer temperature of 100° F. in Provence of France.

I claim:

1. A new and distinct Hybrid Tea rose plant characterized by the following combination of characteristics:

(a) exhibits semi-erect growth habit, (b) abundantly forms on a continuous basis attractive very double long-lasting cream white blossoms having a very strong fragrance that are slightly suffused and bordered with pink, (c) forms vigorous and dense medium green foliage having a semi-glossy aspect that contrasts well with the blossom coloration, and (d) is particularly well suited for growing as attractive ornamentation in parks and gardens;

substantially as herein shown and described.

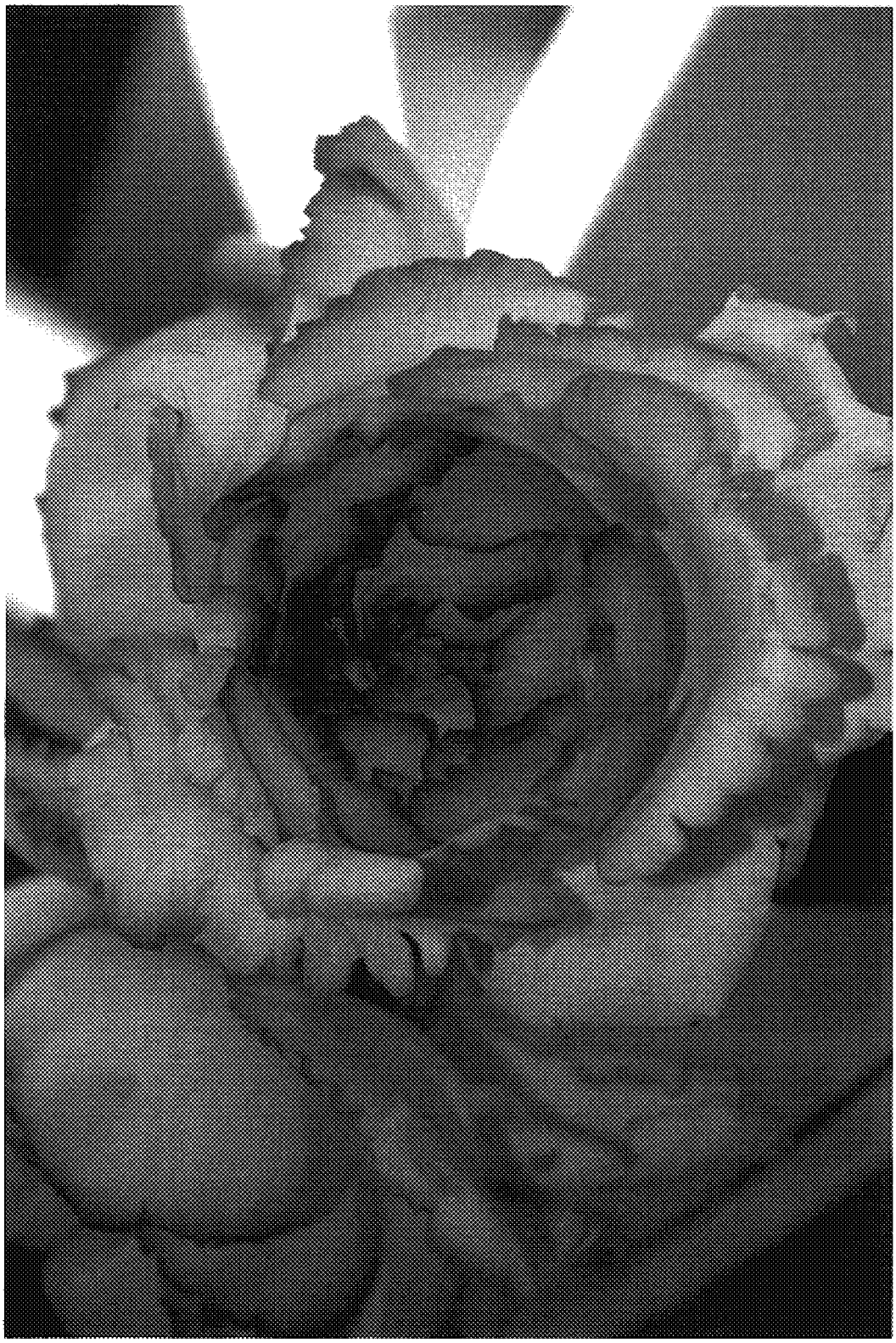

* * * * *